United States Patent
Mainiero et al.

(10) Patent No.: US 6,231,535 B1
(45) Date of Patent: May 15, 2001

(54) SUPPORT FOR MAINTAINING THE HEAD OF A WEARER ERECT WHEN THE WEARER IS IN A SITTING POSITION

(76) Inventors: Joseph Mainiero, 75 Maybrook Rd., Bridgeport, CT (US) 06606; John Mulvihill, 15 Placid St., Trumbull, CT (US) 06611

( * ) Notice: Subject to any disclaimer, the term of this patent is extended or adjusted under 35 U.S.C. 154(b) by 0 days.

(21) Appl. No.: 09/524,586

(22) Filed: Mar. 13, 2000

(51) Int. Cl.$^7$ .............................. A61F 5/00; A47C 20/02
(52) U.S. Cl. .................................. 602/18; 5/636
(58) Field of Search .................... 102/17, 18, 5; 482/10, 108; 128/DIG. 23; 2/468, 45; 5/636, 637, 640, 630, 643, 648; D6/601, 604; D24/183; 601/119–125

(56) References Cited

U.S. PATENT DOCUMENTS

| | | | |
|---|---|---|---|
| D. 396,594 | * 8/1998 | Lefebvre | D6/601 |
| 3,964,474 | 6/1976 | Fox | 128/87 B |
| 4,161,946 | 7/1979 | Zuesse | 128/75 |
| 4,183,583 | 1/1980 | Zuesse | 297/393 |
| 4,232,663 | 11/1980 | Newton | 128/75 |
| 4,285,081 | * 8/1981 | Price | 5/637 |
| 4,325,363 | 4/1982 | Berkeley | 128/75 |
| 4,617,691 | 10/1986 | Monti et al. | 5/434 |
| 4,679,262 | * 7/1987 | Davis et al. | 5/644 |
| 4,700,697 | 10/1987 | Mundell et al. | 128/75 |
| 4,796,315 | * 1/1989 | Crew | 5/630 |
| 5,029,577 | 7/1991 | Sarkozi | 128/87 B |
| 5,060,637 | 10/1991 | Schmid et al. | 128/75 |
| 5,135,455 | * 8/1992 | King | 482/108 |
| 5,211,623 | 5/1993 | Sarkozi | 602/18 |
| 5,303,890 | 4/1994 | Carruth | 248/118 |
| 5,441,479 | * 8/1995 | Chitwood | 602/18 |
| 5,566,682 | * 10/1996 | Yavitz | 128/845 X |
| 5,829,079 | * 11/1998 | Castro | 5/636 |
| 5,971,890 | * 10/1999 | Tyne | 482/10 |
| 6,058,517 | * 5/2000 | Hartunian | 602/18 X |

FOREIGN PATENT DOCUMENTS

2165762 * 4/1986 (GB) ..................................... 602/18

* cited by examiner

Primary Examiner—Mickey Yu
Assistant Examiner—Denise Pothier
(74) Attorney, Agent, or Firm—Richard L. Miller, P. E.

(57) ABSTRACT

A support for maintaining the head of a wearer erect when the wearer is in a sitting position. The support includes a body for maintaining the head of the wearer erect when the wearer is in the sitting position, and a strap that extends from the body for engaging around the neck of the wearer. The body is rigid and defined by a plurality of arcuately-shaped surfaces so configured so as to accommodate for the clavicle, the chin, the upper chest, the neck of the wearer, and a knot of a tie if worn by the wearer.

40 Claims, 1 Drawing Sheet

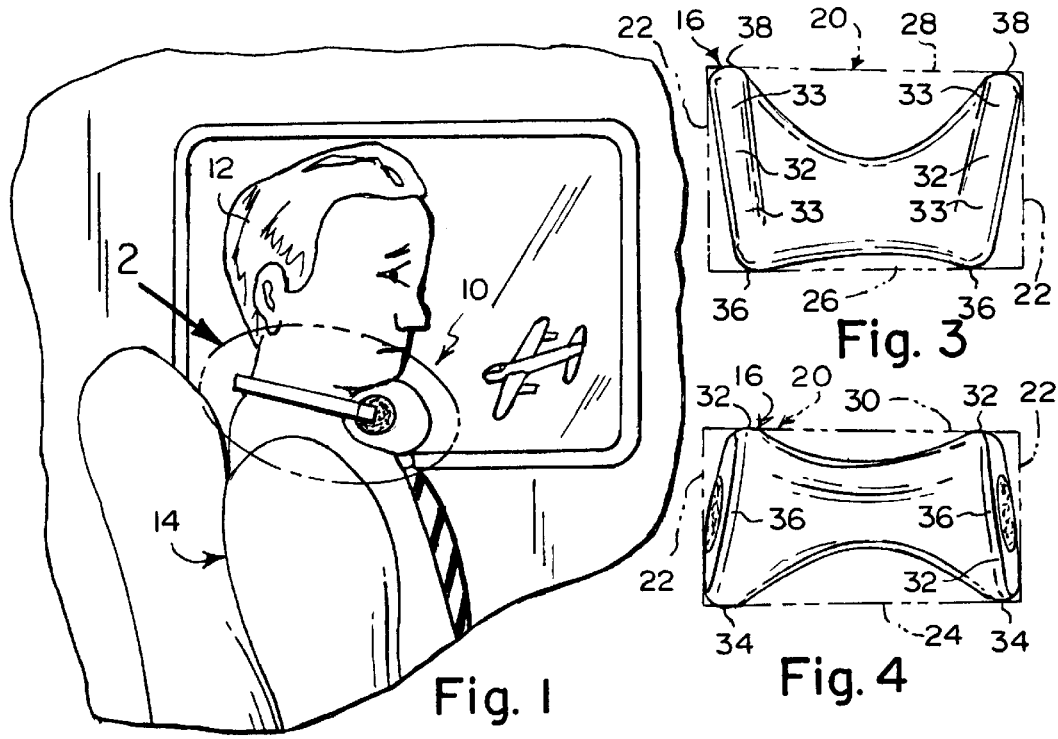
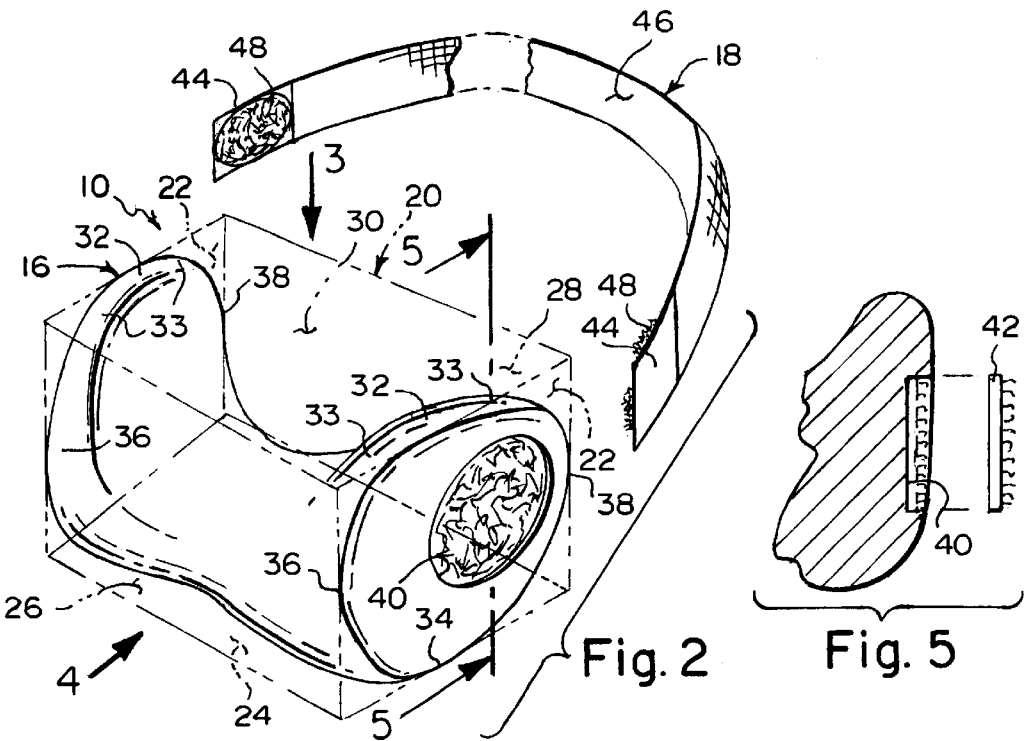

SUPPORT FOR MAINTAINING THE HEAD OF A WEARER ERECT WHEN THE WEARER IS IN A SITTING POSITION

BACKGROUND OF THE INVENTION

1. Field of the Invention

The present invention relates to a support for maintaining the head of a wearer erect. More particularly, the present invention relates to a support for maintaining the head of a wearer erect when the wearer is in a sitting position.

2. Description of the Prior Art

Numerous innovations for head supports have been provided in the prior art that will be described. Even though these innovations may be suitable for the specific individual purposes to which they address, however, they differ from the present invention.

A FIRST EXAMPLE, U.S. Pat. No. 3,964,474 to Fox teaches a cervical collar that is made of plastic foam and includes a thin band of resilient plastic material biasing the foam into an annular shape terminating in opposed rear ends which may be separated to circumferentially expand the collar against the bias of the band for fitting about a patient's neck. A front central top portion of the collar includes a depression and the top surface itself is beveled and shaped in such a manner as to comfortably cradle a patient's front jaw portion and side areas of the head. An outer covering of fabric material may be applied about the collar for purposes of cleanliness and enhancement of the aesthetic appearance of the collar.

A SECOND EXAMPLE, U.S. Pat. No. 4,161,946 to Zuesse teaches a support for maintaining the head in an upright position, as, for example, while resting or sleeping upright in a seat with a back rest. The support includes a forehead-engagement means to resist forward movement of the head. Forehead pressure against this means is transmitted to a nape-of-the-neck-engagement means, which is thereby pressed inwardly upon the rear of the neck. This pressure is then further transmitted by way of a chest-engagement means inwardly upon the sternum. Since the nape of the neck cannot move forward, and the sternum cannot move inward, falling forward of the forehead is precluded. Various ancillary support means can be added to supplement the basic head support. Thus, in some embodiments, the nape-engagement means is extended upwardly to provide an occipital support section which engages the rear of the head and is extended downwardly to form a posterior support section for engaging the upper rear portion of the wearer's back. A shoulder-engaging frame fits across the wearer's shoulders and connects to the posterior support, in one embodiment, lateral supports extend from the shoulder-engaging frame to engage the sides of the wearer's head, and a chin support rises from the chest-engagement means. The complete support can be formed of rigid sections coupled together, or it can be formed of flexible material having an integral air chamber to provide a semi-rigid support. All versions of this head support depend on the basic principle of resisting forward movement of the head by the forehead-engagement means or headband transmitting this pressure to the nape and to the sternum, neither of which moves.

A THIRD EXAMPLE, U.S. Pat. No. 4,183,583 to Zuesse teaches a support for maintaining the head in an upright position while the seat-occupant is seated in a reclining seat. One part of the support is a forehead-engagement means to resist forward movement of the head. Forehead pressure against this means is transmitted by connecting means to a back-plate positioned between the back of the seat-occupant and the back-rest of the seat. With the seat-back-rest partially backward-inclined, and the forehead inclined slightly forward to rest forward against the forehead-engagement means, there is a tendency for the back-plate to rotate forward at the top and backward at the bottom. At the top, it's resisted by the seat-occupant's back, resting backward against the back plate; at the bottom, this rotational tendency is resisted by the seat-back-rest. The back-plate, thus sandwiched between the seat-occupant and the seat, maintains the forehead-engagement means in position to resist the forward-pressure of the resting forward, so that the forehead is prevented from falling forward and downward toward the chest; in other words, the head is thus supported. Ancillary support means can be added to supplement the basic head support above described. Thus, for instance, there may be lateral-support means engaging the shoulders as pat of the connecting means or back-plate, to resist lateral movement of the sleeping or resting head in the event that the seat-occupant (for example) is in transit aboard a vehicle which sways from side to side thus tossing the head left and right. All versions of this head-support depend upon the basic principle of preventing forward-falling of the forehead by transmitting this forward pressure via the connecting means to the back-plate sandwiched between the seat-occupant's back and the seat-back-rest.

A FOURTH EXAMPLE, U.S. Pat. No. 4,232,663 to Newton teaches a cervical collar which is made of a pad of resilient foam material with a scalloped depressed area at the middle of the inside surface of the collar whereby a user's chin is supported in the depression and pressure on a user's throat area is relieved by the reduced thickness provided by the depression.

A FIFTH EXAMPLE, U.S. Pat. No. 4,325,363 to Berkeley teaches a collar which is worn as a neck support for posture training and therapeutic purposes. It is made of a soft spongy plastic material of a shape to fit the contour of the neck, and is reinforced around its rim with a narrow band of a stiff but flexible plastic material. The collar is provided with a plurality of spaced vertical stays which are made of longitudinal tubes containing removable strips of metal therein for controlling the shape and degree of stiffness of the collar. The spaces on the collar between the stays are open to provide ventilation. The collar is held around the neck by strips of adhesive tape such as "Velcro" which join the ends of the collar. Additional and variable support is provided by separate vertical supports which can be attached at various heights and locations on the collar, by "Velcro" type adhesive. These vertical supports are made of a double layer of soft spongy material with metal inserts therein for stiffness and by means of which these supports can be bent into required shapes.

A SIXTH EXAMPLE, U.S. Pat. No. 4,617,691 to Monti et al. teaches a generally rectangular or other suitably shaped support pillow that is adapted to be removably secured around a users neck. A single elongated wedge-shaped pillow segment is provided with fasteners for joining one end to the other. The wedge shape gives increased lateral support to the users neck and head. Worn with the fasteners under the user's chin, it gives increased head and neck support whereas if it is worn with the fasteners behind the users head, it gives increased chin and head support. A three piece versions is also provided and the various pillow segments may be of various sizes. A laminate may be applied to render the support pillow bacteria proof, flame retardant and waterproof while allowing heat and perspiration to escape. A spring-like closure version is also shown.

A SEVENTH EXAMPLE, U.S. Pat. No. 4,700,697 to Mundell et al. teaches a cervical appliance for preventing ventral flexion of the head to reduce the possibility of sudden infant death syndrome and/or adult sleep apnea, both of which have common characteristics which are at least partially obviated with the use of the invention.

A EIGHTH EXAMPLE, U.S. Pat. No. 5,029,577 to Sarkozi teaches a soft neck support collar comprising two offset and attached, tubular ring elements, each element hooking together at their respective ends. Both ring elements contain a soft fill material such as nylon, cotton, polyester, acrylics, foam, foam chips, etc. The combined effect of the fill material together with the tubular configuration, enables the neck to adjust for lateral forward and backward forces during movement. The upper ring element is tapered at each end, so that when these ends are joined together, a space is formed into which the chin can fit, thereby maintaining the neck in a neutral position, and preventing hyperextension. The lower ring element is hooked together at each end, and the rings are offset to enable the lower ring to close at the back of the neck, approximately opposite from the closure of the upper ring element. Hence, the lower ring element functions as a continuous, uniform tubular-shaped ring which does not interfere with movement of the chin. Thus, in the closed configuration, the neck support collar allows for neutral positioning of the chin and neck, and restricts neck, mobility.

A NINTH EXAMPLE, U.S. Pat. No. 5,060,637 to Schmid et al. teaches a disposable cervical collar having an elongated unitary body formed from the plastic core board or similar cellular material, the collar having a frontal section provided with a chin receiving opening, including a chin supporting flap and optionally a chin strip, with a throat opening underlying the chin opening, and a rear section which is slotted at spaced intervals for bending to confirm to the wearer's neck, the rear section having a plastic strap adapted to be adhesively secured to the frontal section to secure the collar in place.

A TENTH EXAMPLE, U.S. Pat. No. 5,211,623 to Sarkozi teaches a soft neck support collar comprising two detached, superposed tubular ring elements which are connected at their respective ends, and are insertably and retractably secured within a flexible and removable outer sleeve. The tubular ring elements contain a soft fill material, and the combined effect of the fill material together with their tubular configuration, enable the collar to appropriately adjust for lateral, forward and backward neck movements. In addition to restricting neck mobility, the collar will self adjust for neutral positioning of the chin and neck. Use of the sleeve enables the use of a greater range of tubular sizes, and provides for adjustable configurations. When necessary or desired, the addition of one or more smaller tubular elements on either side of the tubular ring elements can impart greater stiffness to the ring elements for a given neck position. If desired, a heating and/or cooling element may be insertably secured into the sleeve and between the tubular elements, without requiring additional attachment means, and the heating and/or cooling element will also impart additional reinforcement to the tubular ring elements.

A ELEVENTH EXAMPLE, U.S. Pat. No. 5,303,890 to Carruth teaches a chin rest that is arranged to include a housing having a top wall to include a pad member mounted therein. The housing includes first and second leg tubes mounted to opposed ends of the housing, that in turn include first and second respective extension legs that are provided with support pads to position the organization relative to an underlying support surface permitting an individual to rest the chin thereon during reading and other events when the individual is in the supine position.

It is apparent that numerous innovations for head supports have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a support for maintaining the head of a wearer erect when the wearer is in a sitting position that avoids the disadvantages of the prior art.

ANOTHER OBJECT of the present invention is to provide a support for maintaining the head of a wearer erect when the wearer is in a sitting position that is simple and inexpensive to manufacture.

STILL ANOTHER OBJECT of the present invention is to provide a support for maintaining the head of a wearer erect when the wearer is in a sitting position that is simple to use.

BRIEFLY STATED, YET ANOTHER OBJECT of the present invention is to provide a support for maintaining the head of a wearer erect when the wearer is in a sitting position. The support includes a body for maintaining the head of the wearer erect when the wearer is in the sitting position, and a strap that extends from the body for engaging around the neck of the wearer. The body is rigid and defined by a plurality of arcuately-shaped surfaces so configured so as to accommodate for the clavicle, the chin, the upper chest, the neck of the wearer, and a knot of a tie if worn by the wearer.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 1 is a diagrammatic side elevational view of the present invention in use;

FIG. 2 is an enlarged diagrammatic perspective view of the area generally enclosed by the dotted curve identified by the arrow 2 in FIG. 1 of the present invention;

FIG. 3 is a diagrammatic top plan view taken generally in the direction of arrow 3 in FIG. 2;

FIG. 4 is a diagrammatic front elevational view taken generally in the direction of arrow 4 in FIG. 2; and FIG. 5 is an enlarged diagrammatic cross sectional view taken on line 5—5 in FIG. 3.

LIST OF REFERENCE NUMERALS UTILIZED IN THE DRAWING 10 support for maintaining head 12 of wearer 14 erect when wearer 14 is in sitting position
12 head of wearer 14
14 wearer
16 body for maintaining head 12 of wearer 14 erect when wearer 14 is in sitting position 18 strap for engaging around neck of wearer 14
20 rectangular-parallelepiped-shaped block of body 16
22 pair of end surfaces of rectangular-parallelepiped-shaped block 20 of body 16
24 lowermost surfaces of rectangular-parallelepiped-shaped block 20 of body 16
26 forwardmost surface of rectangular-parallelepiped-shaped block 20 of body 16
28 rearwardmost surface of rectangular-parallelepiped-shaped block 20 of body 16
30 uppermost surface of rectangular-parallelepiped-shaped block 20 of body 16
32 uppermost region of thickened border of each end surface of pair of end surfaces 22 of block 20
33 pair of substantially straight portions of uppermost region 32 of thickened border of each end surface of pair of end surface 22 of block 20
34 lowermost region of thickened border of each end surface of pair of end surfaces 22 of block 20
36 forwardmost region of thickened border of each end surface of pair of end surfaces 22 of block 20
38 rearwardmost region of thickened border of each end surface of pair of end surfaces 22 of block 20
40 recess in each end surface of pair of end surfaces 22 of block 20
42 first portion of hook and loop fasteners on each end surface of pair of end surfaces 22 of block 20
44 pair of free ends of strap 18
46 innermost surface of strap 18
48 second portion of hook and loop fasteners on each free end of pair of free ends 44 of strap 18

DETAILED DESCRIPTION OF THE PREFERRED EMBODIMENT

Referring now to the figures, in which like numerals indicate like parts, and particularly to FIG. 1, the support of the present invention is shown generally at 10 for maintaining the head 12 of a wearer 14 erect when the wearer 14 is in a sitting position.

The overall configuration of the support 10 can best be seen in FIG. 2, and as such, will be discussed with reference thereto.

The support 10 comprises a body 16 for maintaining the head 12 of the wearer 14 erect when the wearer 14 is in the sitting position, and a strap 18 that extends from the body 16 for engaging around the neck of the wearer 14.

The specific configuration of the body 16 can best be seen in FIGS. 2–4, and as such, will be discussed with reference thereto.

For the sake of simplicity, picture the body 16 as a rigid rectangular-parallelepiped-shaped block 20 that has a pair of end surfaces 22 that are free and vertically-oriented, a lowermost surface 24 that is free, horizontally-oriented, and extends from one end surface 22 to the other end surface 22 of the block 20, a forwardmost surface 26 that is free, vertically-oriented, and extends from the one end surface 22 to the other end surface 22 of the block 20, a rearwardmost surface 28 that is free, vertically-oriented, and extends from the one end surface 22 to the other end surface 22 of the block 20, and an uppermost surface 30 that is free, horizontally-oriented, and extends from the one end surface 22 to the other end surface 22 of the block 20, which are deformed into a plurality of arcuately-shaped surfaces so configured so as to accommodate for the clavicle, the chin, the upper chest, the neck of the wearer 14, and a knot of a tie if worn by the wearer 14.

The pair of end faces 22 of the block 20 are flat.

The pair of end faces 22 of the block 20 incline toward each other, from the rearwardmost surface 28 of the block 20 to the forwardmost surface 26 of the block 20 so as to accommodate for the clavicle of the wearer 14.

The pair of end faces 22 of the block 20 incline symmetrically toward each other, from the rearwardmost surface 28 of the block 20 to the forwardmost surface 26 of the block 20.

The pair of end faces 22 of the block 20 further incline toward each other, from the lowermost surface 24 of the block 20 to the uppermost surface 30 of the block 20 so as to further accommodate for the clavicle of the wearer 14.

The pair of end faces 22 of the block 20 further incline symmetrically toward each other, from the lowermost surface 24 of the block 20 to the uppermost surface 30 of the block 20.

The pair of end faces 22 of the block 20 have laterally thickened borders for rigidity, and which are rounded for comfort of the wearer 14.

The rearwardmost surface 28 of the block 20 concaves laterally, toward the forwardmost surface 26 of the block 20, from one end surface 22 to the other end surface 22 of the block 20, so as to accommodate for the neck of the wearer 14, and has a radius of curvature.

The rearwardmost surface 28 of the block 20 concaves laterally, toward the forwardmost surface 26 of the block 20, from the thickened border of the one end surface 22 to the thickened border of the other end surface 22 of the block 20.

The rearwardmost surface 28 of the block 20 concaves laterally and symmetrically, toward the forwardmost surface 26 of the block 20, from the one end surface 22 to the other end surface 22 of the block 20.

The rearwardmost surface 28 of the block 20 convexs vertically, from the lowermost surface 24 of the block 20 to the uppermost surface 30 of the block 20.

The uppermost surface 30 of the block 20 concaves laterally, toward the lowermost surface 24 of the block 20, from the one end surface 22 to the other end surface 22 of the block 20, so as to accommodate for the chin of the wearer 14, and has a radius of curvature.

The uppermost surface 30 of the block 20 concaves laterally, toward the lowermost surface 24 of the block 20, from the thickened border of the one end surface 22 to the thickened border of the other end surface 22 of the block 20.

The uppermost surface 30 of the block 20 concaves laterally and symmetrically, toward the lowermost surface 24 of the block 20, from the one end surface 22 to the other end surface 22 of the block 20.

The uppermost surface 30 of the block 20 convexs vertically, from the forwardmost surface 26 of the block 20 to the rearwardmost surface 28 of the block 20.

The lowermost surface 24 of the block 20 concaves laterally, toward the uppermost surface 30 of the block 20, from the one end surface 22 to the other end surface 22 of the block 20, so as to accommodate for the upper chest of the wearer 14, and has a radius of curvature.

The lowermost surface 24 of the block 20 concaves laterally, toward the uppermost surface 30 of the block 20, from the thickened border of the one end surface 22 to the thickened border of the other end surface 22 of the block 20.

The lowermost surface 24 of the block 20 concaves laterally and symmetrically, toward the uppermost surface 30 of the block 20, from the one end surface 22 to the other end surface 22 of the block 20.

The lowermost surface 24 of the block 20 convexs vertically, from the forwardmost surface 26 of the block 20 to the rearwardmost surface 28 of the block 20.

The forwardmost surface 24 of the block 20 concaves laterally, toward the rearwardmost surface 28 of the block 20, from the one end surface 22 to the other end surface 22 of the block 20, so as to accommodate for a knot of a tie worn by the wearer 14, and has a radius of curvature.

The forwardmost surface 24 of the block 20 concaves laterally, toward the rearwardmost surface 28 of the block 20, from the thickened border of the one end surface 22 to the thickened border of the other end surface 22 of the block 20.

The forwardmost surface 24 of the block 20 concaves laterally and symmetrically, toward the rearwardmost surface 28 of the block 20, from the one end surface 22 to the other end surface 22 of the block 20.

The forwardmost surface 24 of the block 20 convexs vertically, from the lowermost surface 24 of the block 20 to the uppermost surface 30 of the block 20.

The radius of curvature of the rearwardmost surface 28 of the block 20 is greater than the radius of curvature of the forwardmost surface 26 of the block 20.

The radius of curvature of the rearwardmost surface 28 of the block 20 is greater than the radius of curvature of the uppermost surface 30 of the block 20.

The radius of curvature of the rearwardmost surface 28 of the block 20 is greater than the radius of curvature of the lowermost surface 24 of the block 20.

The radius of curvature of the lowermost surface 24 of the block 20 is greater than the radius of curvature of the uppermost surface 30 of the block 20.

The radius of curvature of the lowermost surface 24 of the block 20 is greater than the radius of curvature of the forwardmost surface 26 of the block 20.

The radius of curvature of the uppermost surface 30 of the block 20 is greater than the radius of curvature of the forwardmost surface 26 of the block 20.

The thickened border of each end surface 22 of the block 20 is imaginarily divided into an uppermost region 32, a lowermost region 34, a forwardmost region 36, and a rearwardmost region 38.

The uppermost region 32 of the thickened border of each end surface 22 of the block 20 diverges, toward the lowermost region 34 thereof for preventing interference with the Mylo-Hyoid artery.

The uppermost region 32 of the thickened border of each end surface 22 of the block 20 diverges with a pair of substantially straight portions 33, toward the lowermost region 34 thereof.

The uppermost region 32 of the thickened border of each end surface 22 of the block 20 diverges symmetrically, toward the lowermost region 34 thereof.

The lowermost region 34 of the thickened border of each end surface 22 of the block 20 convexs, toward the uppermost region 32 thereof so as to provide comfort for the sternum of the wearer, and has a radius of curvature.

The forwardmost region 36 of the thickened border of each end surface 22 of the block 20 convexs, toward the rearwardmost region 38 thereof for preventing injury to an arm of the wearer 14 if brushed thereagainst.

The rearwardmost region 38 of the thickened border of each end surface 22 of the block 20 convexs, toward the forwardmost region 36 thereof for preventing interference with the External Carotid artery of the wearer 14, and has a radius of curvature.

The radius of curvature of the lowermost region 34 of the thickened border of each end surface 22 of the block 20 is greater that the radius of curvature of the rearwardmost region 38 thereof, since there is a larger footprint on the upper chest than the neck of the wearer 14.

Each end surface 22 of the block 20 has a recess 40 therein that is disk-shaped and has a depth.

The recess 40 in each end surface 22 of the block 20 is disposed concentrically to the convex of the rearwardmost region 36 of the thickened border of each end surface 22 of the block 20.

Each end surface 22 of the block 20 further has a first portion of hook and loop fasteners 42 that is disk-shaped and disposed in the recess 40 in the associated end surface 22 of the block 20.

The first portion of hook and loop fasteners 42 of each end surface 22 of the block 20 fills the recess 40 in the associated each end surface 22 of the block 20, to about half the depth thereof, so as to allow the first portion of hook and loop fasteners 42 of the associated end surface 22 of the block 20 to be recessed in the recess 40 in the associated end surface 22 of the block 20.

The specific configuration of the strap 18 and its interface with the body 16 can best be seen in FIGS. 2 and 5, and as such, will be discussed with reference thereto.

The strap 18 is slender, elongated, and has a pair of free ends 44 and an innermost surface 46.

Each free end 44 of the strap 18 has a second portion of hook and loop fasteners 48 thereon that is disposed on the innermost surface 46 thereof.

The second portion of hook and loop fasteners 48 on each free end 44 of the strap 18 matingly engages with the first portion of hook and loop fasteners 42 in the recess 40 of the associated end surface 22 of the block 20.

The second portion of hook and loop fasteners 48 on each free end 44 of the strap 18 is disk-shaped and fills the remaining half of the depth of the recess 40 in the associated each end surface 22 of the block 20 so as to allow the second portion of hook and loop fasteners 48 on each free end 44 of the strap 18 to be recessed in the recess 40 in the associated end surface 22 of the block 20 for preventing at least one of the first portion of hook and loop fasteners 42 and the second portion of hook and loop fasteners 48 from attracting debris, such as hair, dandruff, dead skin, or the like.

It will be understood that each of the elements described above, or two or more together, may also find a useful application in other types of constructions differing from the types described above.

While the invention has been illustrated and described as embodied in a support for maintaining the head of a wearer erect when the wearer is in a sitting position, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A support for maintaining the head of a wearer erect when the wearer is in a sitting position, said support comprising:
   a) a body for maintaining the head of the wearer erect when the wearer is in the sitting position; said body being a block being rigid and having:
      i) a pair of end surfaces being free and vertically-oriented; said pair of end faces of said block having laterally thickened borders for rigidity, and being rounded for comfort of the wearer; said thickened border of each end surface of said block being divided into:
         A) an uppermost region;
         B) a lowermost region; said lowermost region of said thickened border of each end surface of said block being convex for providing comfort for the sternum of the wearer, and having a radius of curvature;
         C) a forwardmost region; and
         D) a rearwardmost region; said rearwardmost region of said thickened border of each end surface of said block being convex for preventing interference with the External Carotid artery of the wearer, and having a radius of curvature; said radius of curvature of said lowermost region of said thickened border of each end surface of said block being greater than said radius of curvature of said rearwardmost region thereof, since there is a larger footprint on the upper chest than the neck of the wearer;
      ii) a lowermost surface being free, horizontally-oriented, and extending from one end surface to the other end surface of said block;
      iii) a forwardmost surface being free, vertically-oriented, and extending from said one end surface to said other end surface of said block;
      iv) a rearwardmost surface being free, vertically-oriented, and extending from said one end surface to said other end surface of said block: and
      v) an uppermost surface being free, horizontally-oriented, and extending from said one end surface to said other end surface of said block; and
   b) a strap extending from said block for engaging around the neck of the wearer.

2. The support as defined in claim 1, wherein said pair of end faces of said block are flat.

3. The support as defined in claim 1, wherein said pair of end faces of said block incline toward each other, from said rearwardmost surface of said block to said forwardmost surface of said block so as to accommodate for the clavicle of the wearer.

4. The support as defined in claim 1, wherein said pair of end faces of said block incline symmetrically toward each other, from said rearwardmost surface of said block to said forwardmost surface of said block.

5. The support as defined in claim 1, wherein said pair of end faces of said block incline toward each other, from said lowermost surface of said block to said uppermost surface of said block, so as to accommodate for the clavicle of the wearer.

6. The support as defined in claim 1, wherein said pair of end faces of said block incline symmetrically toward each other, from said lowermost surface of said block to said uppermost surface of said block.

7. The support as defined in claim 1, wherein said rearwardmost surface of said block concaves laterally, toward said forwardmost surface of said block, from said one end surface to said other end surface of said block, so as to accommodate for the neck of the wearer, and has a radius of curvature.

8. The support as defined in claim 7, wherein said uppermost surface of said block concaves laterally, toward said lowermost surface of said block, from said one end surface to said other end surface of said block, so as to accommodate for the chin of the wearer, and has a radius of curvature.

9. The support as defined in claim 8, wherein said lowermost surface of said block concaves laterally, toward said uppermost surface of said block, from said one end surface to said other end surface of said block, so as to accommodate for the upper chest of the wearer, and has a radius of curvature.

10. The support as defined in claim 9, wherein said forwardmost surface of said block concaves laterally, toward said rearwardmost surface of said block, from said one end surface to said other end surface of said block, so as to accommodate for a knot of a tie worn by the wearer, and has a radius of curvature.

11. The support as defined in claim 10, wherein said radius of curvature of said rearwardmost surface of said block is greater than said radius of curvature of said forwardmost surface of said block.

12. The support as defined in claim 10, wherein said radius of curvature of said lowermost surface of said block is greater than said radius of curvature of said forwardmost surface of said block.

13. The support as defined in claim 12, wherein said radius of curvature of said uppermost surface of said block is greater than said radius of curvature of said forwardmost surface of said block.

14. The support as defined in claim 9, wherein said radius of curvature of said rearwardmost surface of said block is greater than said radius of curvature of said lowermost surface of said block.

15. The support as defined in claim 14, wherein said radius of curvature of said lowermost surface of said block is greater than said radius of curvature of said uppermost surface of said block.

16. The support as defined in claim 8, wherein said radius of curvature of said rearwardmost surface of said block is greater than said radius of curvature of said uppermost surface of said block.

17. The support as defined in claim 1, wherein said rearwardmost surface of said block concaves laterally, toward said forwardmost surface of said block, from said thickened border of said one end surface to said thickened border of said other end surface of said block.

18. The support as defined in claim 1, wherein said rearwardmost surface of said block concaves laterally and symmetrically, toward said forwardmost surface of said block, from said one end surface to said other end surface of said block.

19. The support as defined in claim 1, wherein said rearwardmost surface of said block convexs vertically, from said lowermost surface of said block to said uppermost surface of said block.

20. The support as defined in claim 1, wherein said uppermost surface of said block concaves laterally, toward said lowermost surface of said block, from said thickened border of one end surface to said thickened border of said other end surface of said block.

21. The support as defined in claim 1, wherein said uppermost surface of said block concaves laterally and symmetrically, toward said lowermost surface of said block, from said one end surface to said other end surface of said block.

22. The support as defined in claim 1, toward said lowermost surface of said block, from said forwardmost surface of said block to said rearwardmost surface of said block.

23. The support as defined in claim 1, wherein said lowermost surface of said block concaves laterally, toward said uppermost surface of said block, from said thickened border of said one end surface to said thickened border of said other end surface of said block.

24. The support as defined in claim 1, wherein said lowermost surface of said block concaves laterally and symmetrically, toward said uppermost surface of said block, from said one end surface to said other end surface of said block.

25. The support as defined in claim 1, wherein said lowermost surface of said block convexs vertically, toward said uppermost surface of said block, from said forwardmost surface of said block to said rearwardmost surface of said block.

26. The support as defined in claim 1, wherein said forwardmost surface of said block concaves laterally, toward said rearwardmost surface of said block, from said thickened border of said one end surface to said thickened border of said other end surface of said block.

27. The support as defined in claim 1, wherein said forwardmost surface of said block concaves laterally and symmetrically, toward said rearwardmost surface of said block, from said one end surface to said other end surface of said block.

28. The support as defined in claim 1, wherein said forwardmost surface of said block convexs vertically, from said lowermost surface of said block to said uppermost surface of said block.

29. The support as defined in claim 1, wherein said uppermost region of said thickened border of each end surface of said block diverges, toward said lowermost region thereof for preventing interference with the Mylo-Hyoid artery.

30. The support as defined in claim 1, wherein said uppermost region of said thickened border of each end surface of said block diverges with a pair of substantially straight portions, toward said lowermost region thereof.

31. The support as defined in claim 1, wherein said uppermost region of said thickened border of each end surface of said block diverges symmetrically, toward said lowermost region thereof.

32. The support as defined in claim 1, wherein said forwardmost region of said thickened border of each end surface of said block is convex.

33. The support as defined in claim 1, wherein each end surface of said block has a recess therein that is disk-shaped and has a depth.

34. The support as defined in claim 33, wherein said recess in each end surface of said block is disposed concentrically to said rearwardmost region of said thickened border of each end surface of said block.

35. The support as defined in claim 33, wherein each end surface of said block further has a first portion of hook and loop fasteners that is disk-shaped and disposed in said recess in an associated end surface of said block.

36. The support as defined in claim 35, wherein said first portion of hook and loop fasteners of each end surface of said block fills said recess in said associated each end surface of said block, to about half said depth thereof, so as to allow said first portion of hook and loop fasteners of said associated end surface of said block to be recessed in said recess in said associated end surface of said block.

37. The support as defined in claim 36, wherein said strap is slender, elongated, and has:
   a) a pair of free ends; and
   b) an innermost surface.

38. The support as defined in claim 37, wherein each free end of said strap has a second portion of hook and loop fasteners thereon that is disposed on said innermost surface thereof.

39. The support as defined in claim 38, wherein said second portion of hook and loop fasteners on each free end of said strap matingly engages with said first portion of hook and loop fasteners in said recess of said associated end surface of said block.

40. The support as defined in claim 38, wherein said second portion of hook and loop fasteners on each free end of said strap is disk-shaped and fills the remaining half of said depth of said recess in said associated end surface of said block so as to allow said second portion of hook and loop fasteners on each free end of said strap to be recessed in said recess in said associated end surface of said block for preventing at least one of said first portion of hook and loop fasteners and said second portion of hook and loop fasteners from attracting debris.

* * * * *